US006465247B1

(12) United States Patent
Weissman et al.

(10) Patent No.: US 6,465,247 B1
(45) Date of Patent: Oct. 15, 2002

(54) MAMMALIAN MYELOID PROGENITOR CELL SUBSETS

(75) Inventors: Irving L. Weissman, Redwood City, CA (US); David Jeffrey Traver, West Roxbury, MA (US); Koichi Akashi, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 19 days.

(21) Appl. No.: 09/607,529

(22) Filed: Jun. 29, 2000

(51) Int. Cl.$^7$ .............................. C12N 5/06; C12N 5/08
(52) U.S. Cl. ..................... 435/325; 424/93.2; 424/93.7; 435/2; 435/354; 435/355; 435/372
(58) Field of Search ........................... 435/2, 325, 354, 435/355, 372; 424/93.2, 93.7

(56) References Cited

U.S. PATENT DOCUMENTS

| | | | |
|---|---|---|---|
| 5,808,002 A | 9/1998 | Bühring | 530/388.22 |
| 5,821,108 A | 10/1998 | Akashi et al. | 435/240.2 |
| 5,843,633 A | 12/1998 | Yin et al. | 435/2 |
| 5,905,041 A | 5/1999 | Beug et al. | 435/372 |

FOREIGN PATENT DOCUMENTS

| WO | WO 99/10478 | 3/1999 |
|---|---|---|
| WO | 99/10478 | * 3/1999 |

OTHER PUBLICATIONS

Akashi et al. (1997), "Bcl–2 Rescues T Lymphocytes in Interleukin–7 Receptor–Deficient Mice." *Cell*, vol. 89:1033–1041.
Enver et al. (Jul. 15, 1998), "De Stem Cells Play Dice?" *Blood*, vol. 92(2):348–351.
Georgopoulos et al. (1997), "The Role of the Ikaros Gene in Lymphocyte Development and Homeostasis." *Annu. Rev. Immunol.*, vol. 15:155–176.
Heimfeld et al. (Nov. 1991), "The in vitro Response of Phenotypically Defined Mouse Stem Cells and Myeloerythroid Progenitors to Single or Multiple Growth Factors." *Proc. Natl. Acad. Sci. USA*, vol. 88:9902–9906.
Metcalf, Donald (Jul. 15, 1998), "Lineage Commitment and Maturation in Hematopoietic Cells: The Case for Extrinsic Regulation." *Blood*, vol. 92(2):345–352.
Kondo et al. (Nov. 28, 1997), "Identification of Clonogenic Common Lymphoid Progenitors in Mouse Bone Marrow." *Cell*, vol. 91:661–672.
Magli et al. (Feb. 11, 1982), "Transient Nature of Early Hematopoeitic Spleen Colonies." *Nature*, vol. 295:527–529.
Miyamoto et al. (Jun. 1, 1996), "Persistence of Multipotent Progenitors Expressing *AML1/ETO* Transcripts in Long-Term Remission Patients with t(8.21) Acute Myelogenous Leukemia." *Blood*, vol. 87(11):4789–4796.
Morrison et al. (Sep. 1996), "The Aging of Hematopoietic Stem Cells." *Nature Medicine*, vol. 2(9):1011–1016
Morrison et al. (Nov. 1994), "The Long–Term Repopulating Subset of Hematopoietic Stem Cells is Deterministic and Isolatable by Phenotype." *Immunity*, vol. 1:661–673. .

Ogawa, Makio (Jun. 1, 1993), "Differentiation and Proliferation of Hematopoietic Stem Cells." *Blood*, vol. 81(11):2844–2853.
Orkin, Stewart (1996), "Development of the Hematopoietic System." *Current Biology*, vol. 6:597–602.
Pevny et al. (Jan. 17, 1991), "Erythroid Differentiation in Chimaeric Mice Blocked by a Targeted Mutation in the Gene for Transcription Factor GATA–1." *Nature*, vol. 349:257–260.
Shivdasani et al. (1997), "A Lineage–Selective Knockout Establishes the Critical Role of Transcription Factor GATA–1 in Megakaryocyte Growth and Platelet Development." *The EMBO Journal*, vol. 16(13):3965–3973.
Siminovitch et al. (Dec. 1963), "The Distribution of Colony–Forming Cells Among Spleen Colonies." *Journal of Cellular and Comparative Physiology*, vol. 62(3):327–336.
Singh, Harinder (1996), "Gene Targeting Reveals a Hierarchy of Transcription Factors Regulating Specification of Lymphoid Cell Fates." *Current Biology*, vol. 8:160–165.
Spangrude et al. (Jul. 1, 1988), "Purification and Characterization of Mouse Hematopoietic Stem Cells." *Science*, vol. 241:58–62.
Suda et al. (Aug. 1984), "Analysis of Differentiation of Mouse Hematopoietic Stem Cells in Culture by Sequential Replating of Paired Progenitors." *Blood*, vol. 64(2):393–399.
Traver et al. (Jul. 1998), "Mice Defective in Two Apoptosis Pathways in the Myeloid Lineage Develop Acute Myeloblastic Leukemia." *Immunity*, vol. 9:47–57.
Uchida et al. (Jun. 15, 1994), "Rapid and Sustained Hematopoietic Recovery in Lethally Irradiated Mice Transplaned with Purified Thy—$1.1^{lo}$ Lin$^-$ Sca–$1^+$ Hematopoietic Stem Cells." *Blood*, vol. 83(12):3758–3779.
Zon et al. (Dec. 1991), "Activation of the Erythropoietin Receptor Promoter by Transcription Factor GATA–1." *Proc. Natl. Acad. Sci. USA*, vol. 88:10638–10641.

* cited by examiner

*Primary Examiner*—David Saunders
(74) *Attorney, Agent, or Firm*—Pamela J. Sherwood; Bozicevic, Field & Francis LLP

(57) ABSTRACT

A substantially enriched mammalian hematopoietic cell subpopulation is provided, which is characterized by progenitor cell activity for myeloid lineages, but lacking the potential to differentiate into lymphoid lineages. This population is further divided into specific myeloid progenitor subsets, including a common myeloid progenitor cells (CMP), megakaryocyte/erythroid progenitor cells (MEP) and granulocyte/monocyte lineage progenitor (GMP). Methods are provided for the isolation and culture of these subpopulations. The CMP population gives rise to all myeloid lineages, and can give rise to the two additional and isolatable progenitor populations that are exclusively committed to either the erythroid/megakaryocytic or myelomonocytic lineages. The cell enrichment methods employ reagents that specifically recognize CDw127 (IL-7 receptor α); CD117 (c-kit) protein, in conjunction with other markers expressed on lineage committed cells. These cells give rise to a variety of myeloid cells, including megakaryocytes, granulocytes, dendritic cells and erythroid cells, as evidenced by their growth and differentiation in vitro and in vivo.

9 Claims, 5 Drawing Sheets

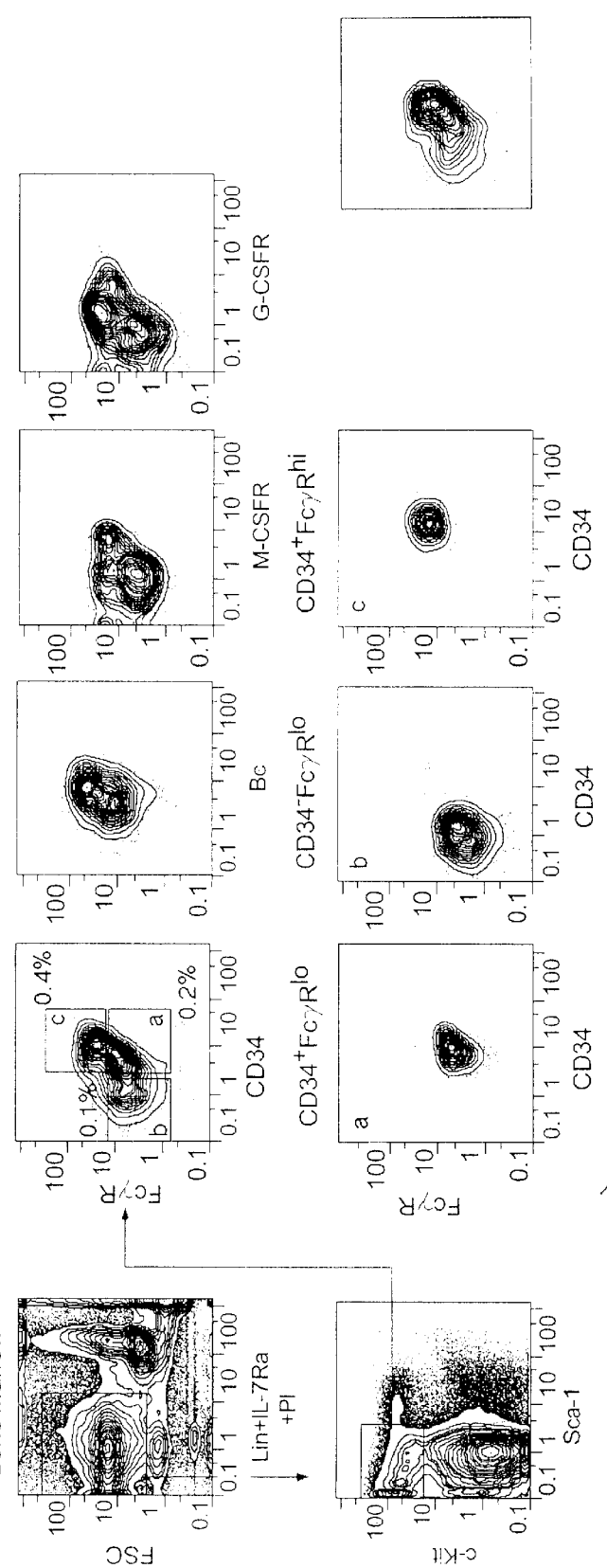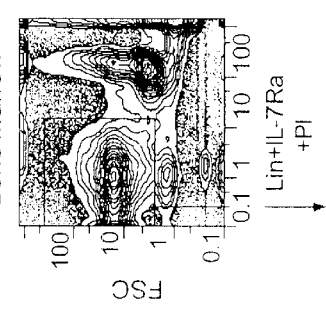

MAMMALIAN MYELOID PROGENITOR CELL SUBSETS

CROSS-REFERENCE TO RELATED APPLICATIONS

This application claims benefit to Provisional Application Ser. No. 60/141,421, filed Jun. 29, 1999.

GOVERNMENT SUPPORT

This invention was made with Government support under contract CA42551 awarded by the National Institutes of Health. The Government has certain rights in this invention.

BACKGROUND

The mammalian immune system plays a vital role in protection from disease, but its effectiveness rests on a fragile balance of power. Excessive or inappropriate responses result in autoimmune disease, while a failure to respond results in immunodeficiency. When such conditions occur, therapeutic intervention may be required. However, it is not easy to successfully manipulate such a complex system.

The mature cells of the immune system, T cells, B cells and natural killer cells, continually differentiate from hematopoietic stem cells, through a series of cell divisions. It is believed that after each cell division the developmental potential of the daughter cells is either maintained or further restricted relative to the parent, never expanded. One therefore observes that pluripotential stem cells give rise to multi-lineage committed progenitor cells, which give rise to specific lineages and finally mature cells. The coordinated changes of cellular properties leading to irreversible restriction of lineage commitment may be due to sequential activation or silencing of various genes.

The phenotype of long-lived pluripotential hematopoietic stem cells has been described. However, the identification of intermediate bipotent or oligopotent progenitors has been difficult, since the evaluation of differentiating potential may be perturbed by a possible failure for the cells to read out detectable differentiation to particular lineages, which may be due to failure in reaching suitable microenvironments in vivo, an insufficient expansion for detection in vivo, or the stochastic nature of lineage commitment, at least in vitro.

The use of pluripotential of lineage committed progenitor cells circumvents many of the problems that would arise from the transfer of mature cells. However, such progenitor cells must be separated from other hematopoietic cells. Separation requires identification of the cell and characterization of phenotypic differences that can be utilized in a separation procedure. Cells that are amenable to genetic manipulation are particularly desirable.

Relevant Literature

A number of review articles have been published addressing the phenotype of cells in hematopoietic lineages. Overall development of the hematolymphoid system is discussed in Orkin (1996) Curr. Opin. Genet. Dev. 6:597–602. The role of transcriptional factors in the regulation of hematopoietic differentiation is discussed in Georgopoulos et al. (1997) Annu. Rev. Immunol. 15:155–176; and Singh (1996) Curr. Opin. Immunol. 8:160–165.

References

Morrison, S. J. & Weissman, I. L. The long-term repopulating subset of hematopoietic stem cells is deterministic and isolatable by phenotype. *Immunity* 1, 661–673 (1994).

Spangrude, G. J., Heimfeld, S. & Weissman, I. L. Purification and characterization of mouse hematopoietic stem cells. *Science* 241, 58–62 (1988)

Kondo, M., Weissman, I. L. & Akashi, K. Identification of clonogenic common lymphoid progenitors in mouse bone marrow. *Cell* 91, 661–672 (1997).

Akashi, K., Kondo, M., von Freeden-Jeffry, U., Murray, R. & Weissman, I. L. Bcl-2 rescues T lymphopoiesis in interleukin-7 receptor-deficient mice. *Cell* 89, 1033–1041 (1997).

Ogawa, M. Differentiation and proliferation of hematopoietic stem cells. *Blood* 81, 2844–2853 (1993).

Heimfeld, S., Hudak, S., Weissman, I. & Rennick, D. The in vitro response of phenotypically defined mouse stem cells and myeloerythroid progenitors to single or multiple growth factors. *Proc Natl Acad Sci USA* 88, 9902–9906 (1991).

Siminovitch, L., McCulloch, E. A., and Till, J. E. The distribution of colony-forming cells among spleen colonies. *J. cell comp. Physiol.* 62, 327–336 (1963).

Magli, M. C., Iscove, N. N. & Odartchenko, N. Transient nature of early hematopoietic spleen colonies. *Nature* 295, 527–529 (1982).

Uchida, N., Aguila, H. L., Fleming, W. H., Jerabek, L. & Weissman, I. L. Rapid and sustained hematopoietic recovery in lethally irradiated mice transplanted with purified Thy-1.1lo Lin-Sca-1+hematopoietic stem cells. *Blood* 83, 3758–3779 (1994).

Shivdasani, R. A., Fujiwara, Y., McDevitt, M. A. & Orkin, S. H. A lineage-selective knockout establishes the critical role of transcription factor GATA-1 in megakaryocyte growth and platelet development. *Embo J* 16, 3965–3973 (1997).

Pevny, L., et al. Erythroid differentiation in chimeric mice blocked by a targeted mutation in the gene for transcription factor GATA-1. *Nature* 349, 257–260 (1991).

Zon, L. I., Youssoufian, H., Mather, C., Lodish, H. F. & Orkin, S. H. Activation of the erythropoietin receptor promoter by transcription factor GATA-1. *Proc Natl Acad Sci USA* 88, 10638–10641 (1991).

Suda, J., Suda, T. & Ogawa, M. Analysis of differentiation of mouse hemopoietic stem cells in culture by sequential replating of paired progenitors. *Blood* 64, 393–399 (1984).

Enver, T., Heyworth, C. M. & Dexter, T. M. Do stem cells play dice! *Blood* 92, 348–351; discussion 352 (1998).

Metcalf, D. Lineage commitment and maturation in hematopoietic cells: the case for extrinsic regulation. *Blood* 92, 345–347; discussion 352 (1998).

Traver, D., Akashi, K., Weissman, I. L. & Lagasse, E. Mice defective in two apoptosis pathways in the myeloid lineage develop acute myeloblastic leukemia. *Immunity* 9, 47–57 (1998).

Morrison, S. J., Wandycz, A. M., Akashi, K., Globerson, A. & Weissman, I. L. The aging of hematopoietic stem cells. *Nat Med* 2, 1011–1016 (1996).

Miyamoto, T., et al. Persistence of multipotent progenitors expressing AML1/ETO transcripts in long-term remission patients with t(8;21) acute myelogenous leukemia. *Blood* 87, 4789–4796 (1996).

SUMMARY OF THE INVENTION

A substantially enriched mammalian hematopoietic cell subpopulation is provided, which is characterized by progenitor cell activity for myeloid lineages, but lacking the potential to differentiate into lymphoid lineages. This population is called the common myeloid progenitor cell (CMP). Methods are provided for the isolation and culture of these subpopulations. The CMP population gives rise to all myeloid lineages, and can give rise to two additional progenitor populations that are exclusively committed to either the erythroid/megakaryocytic (MEP) or myelomonocytic lineages (GMP). Both MEP and GMP can be substantially enriched, isolated and cultured. The three progenitor populations are useful in transplantation, for experimental evaluation, and as a source of lineage and cell specific products, including mRNA species useful in identifying genes specifically expressed in these cells, and as targets for the discovery of factors or molecules that can affect them.

BRIEF DESCRIPTION OF THE DRAWINGS

FIG. 1. Identification of myeloid progenitors in mouse bone marrow. (A) Live, lineage$^-$ IL-7R$^-$ cells were gated and visualized for expression of the c-Kit and Sca-1 surface markers. (B) The Lin$^-$ IL-7R$^-$ Sca-1$^-$ c-Kit$^+$ fraction was subdivided into FcγR$^{lo}$ CD34$^+$ (a), FcγR$^{lo}$ CD34$^-$ (b), and FcγR$^{hi}$ CD34$^+$ (c) populations. Expression of the G-CSFR, M-CSFR and βc was exclusively seen in the FcγR$^{hi}$CD34$^+$ population. (C) Reanalysis of the sorted FcγR$^{lo}$ CD34$^+$, FcγR$^{lo}$CD34$^-$ and FcγR$^{hi}$CD34$^+$ populations. All populations were double-sorted for in vivo and in vitro assays.

DESCRIPTION OF THE SPECIFIC EMBODIMENTS

Figure 2A:
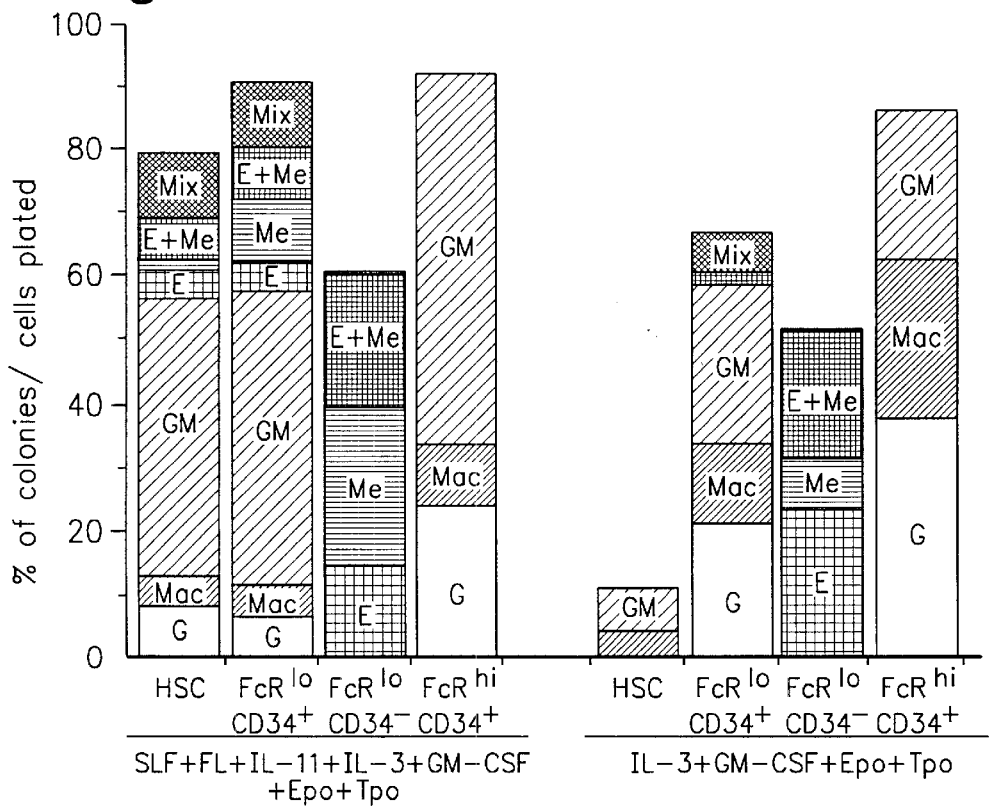
FIG. 2. Clonogenic myeloid colony readout in methylcellulose. (A)288 wells receiving a single cell each were scored from each sorted progenitor population. The FcγR$^{lo}$ CD34$^+$cells as well as HSC formed various myeloid colonies including CFU-GEMM, whereas the FcγR$^{lo}$ CD34$^-$ and FcγR$^{hi}$CD34$^+$ populations gave rise only to Meg/E and G/M colonies, respectively (left). All myeloid progenitor populations did not require SLF, FL, or IL-11 for colony formation (right). (B) Meg/E colony formation from the FcγR$^{lo}$ CD34$^{+/-}$ fractions was completely dependent upon Epo and Tpo. CD34$^+$ myeloid progenitors form myelomonocytic colonies in the presence of only IL-3 and GM-CSF (right).

Mammalian hematopoietic progenitor cells that are committed to myeloid lineages are provided. These cells are subdivided into three distinct subsets: a common myeloid progenitor cell (CMP); a granulocyte monocyte (GMP) committed progenitor cell; and an erythroid/megakaryocyte (MEP) committed progenitor cell. The CMP gives rise to the other two subsets.

The CMP population is useful in transplantation to provide a recipient with myeloid cells, including megakaryocytes, platelets and erythroid cells, in addition to monocytes and granulocytes; for drug screening; experimental models of hematopoietic differentiation and interaction; screening in vitro assays to define growth and differentiation factors, and to characterize genes involved in myeloid development and regulation; and the like. The native cells may be used for these purposes, or they may be genetically modified to provide altered capabilities.

CMPs are separated from a complex mixture of cells by using reagents that specifically recognize markers on the cell surface, including CDw127 (IL-7 receptor α); CD117 (c-kit) protein, and a cocktail of markers expressed on lineage committed cells. Murine myeloid progenitor cells of the invention are also characterized as lacking expression of Sca-1 (Ly-6E and Ly-6A). In human cells the level of staining for CD34 and c-kit is low. The three progenitor cell subsets are all characterized as IL-7Rα negative, sca-1 negative, lineage negative, and c-kit high.

The population of cells that is Lin IL-7R$^-$ Sca-1$^-$ c-Kit$^+$ fraction may be subdivided into the progenitor populations of the invention on the basis of expression of CD34, and the Fcγ receptor (FcγR). The FcγR$^{lo}$ CD34$^+$ population provides the common myeloid progenitor. The FcγR$^{lo}$ CD34$^-$ provides the MEP progenitor population; and the FcγR$^{hi}$ CD34$^+$ population provides the GMP progenitor subset.

In the presence of steel factor (SLF), flt-3 ligand (FL), interleukin (IL)-3, IL-11, GM-CSF, thrombopoietin (Tpo) and erythropoietin (Epo), the FcγR$^{lo}$ CD34$^+$ cells give rise to various types of myeloerythroid colonies, including CFU-GEMMeg, burst-forming unit-erythroid (BFU-E), CFU-megakaryocytes (CFU-Meg), CFU-granulocyte/macrophage (CFU-GM), CFU-granulocyte (CFU-G) and CFU-macrophage (CFU-M).

The FcγR$^{hi}$ CD34$^+$ population generates CFU-M, CFU-G, or CFU-GM colonies containing macrophages and/or granulocytes in response to the above growth factors. In contrast, FcγR$^{lo}$ CD34$^-$ cells give rise to CFU-Meg, BFU-E, or CFU-MEP colonies containing only megakaryocytes and/or erythrocytes in response to IL-3, GM-CSF, Tpo and Epo, but do not form colonies in the absence of Tpo and Epo. All three myeloid progenitor populations do not require "early-acting cytokines" such as SLF, FL and IL-11 to initiate colony formation.

All of these progenitors are capable of rapid differentiation activity in vivo. CMP cells give rise to Gr-1+/Mac-1+ myelomonocytic cells and megakaryocytic colonies, as well as TER119+erythroid cells in spleen and bone marrow. The GMP progenitor population gives rise to Gr-1+/Mac-1+ cells; and the MEP progenitor population to megakaryocytes and erythroid cells.

Methods for enrichment of myeloid progenitor cell subsets are provided. The enriched cell population will usually have at least about 90% cells of the selected phenotype, more usually at least 95% cells of the selected phenotype. The subject cell populations are separated from other cells, e.g. hematopoietic cells, on the basis of specific markers, which are identified with affinity reagents, e.g. monoclonal antibodies.

The myeloid progenitor subsets are isolated from any source of hematopoietic progenitor cells, which may be fetal, neonatal, juvenile or adult, including bone marrow, spleen, liver, umbilical cord blood, peripheral blood, mobilized peripheral blood, yolk sac, etc. For autologous or allogeneic transplantation, bone marrow and mobilized peripheral blood are preferred starting materials. For peripheral blood, progenitor cells are mobilized from the marrow compartment into the peripheral bloodstream after treatment with chemotherapy; G-CSF or GM-CSF, or both. A number of single and combination chemotherapeutic agents have been used to mobilize PBPCs. In administering these agents, a balance must be found in all cases between effective PBPC mobilization and possible damage to the hematopoietic stem cell pool and overall patient tolerance. Paclitaxel has been found to effectively mobilize PBPCs without damaging the stem cell pool. A review of peripheral blood stem cells may be found in Shpall et al. (1997) *Annu Rev Med* 48:241–251, and the characterization of stem cell mobilization in Moog et al. (1998) *Ann Hematol* 77(4):143–7. As an alternative source of cells, hematopoietic stem cells, as described in U.S. Pat. No. 5,061,620, issued on Oct. 29, 1991; and U.S. Pat. No. 5,087,570, issued Feb. 11, 1992, may be cultured in vivo or in vitro to provide a source of cells.

The progenitor cells may be obtained from any mammalian species, e.g. equine, bovine, porcine, canine, feline, rodent, e.g. mice, rats, hamster, primate, etc., particularly human. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−180° C.) indefinitely.

The subject myeloid progenitor cells are characterized by their expression of cell surface markers. For several of these markers, the expression is low or intermediate in level. While it is commonplace to refer to cells as "positive" or "negative" for a particular marker, actual expression levels are a quantitative trait. The number of molecules on the cell surface can vary by several logs, yet still be characterized as "positive". Characterization of the level of staining permits subtle distinctions between cell populations.

The staining intensity of cells can be monitored by flow cytometry, where lasers detect the quantitative levels of fluorochrome (which is proportional to the amount of cell surface antigen bound by the antibodies). Flow cytometry, or FACS, can also be used to separate cell populations based on the intensity of antibody staining, as well as other parameters such as cell size and light scatter. Although the absolute level of staining may differ with a particular fluorochrome and antibody preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest cells in a bone marrow sample are designated as 4 logs more intense than the cells having the lowest level of staining. When displayed in this manner, it is clear that the cells falling in the highest log of staining intensity are bright, while those in the lowest intensity are negative. The "low" staining cells, which fall in the 2–3rd log of staining intensity, have properties that are unique from the negative and positive cells. An alternative control may utilize a substrate having a defined density of antigen on its surface, for example a fabricated bead or cell line, which provides the positive control for intensity. The "low" designation indicates that the level of staining is above the brightness of an isotype matched control, but is not as intense as the most brightly staining cells normally found in bone marrow.

The subject myeloid progenitor subsets are characterized by their expression of growth factor receptors. In addition to providing a convenient marker for separation, the cognate ligands are biologically active on CMPs. The subject cells express high levels of c-kit (CD117) on their cell surface. Antibodies that specifically bind c-kit in humans, mice, rats, etc. are known in the art. Alternatively, the c-kit ligand, steel factor (Slf) may be used to identify cells expressing c-kit.

The myeloid progenitor subsets also have the phenotype of lacking expression of lineage specific markers, exemplified by B220, CD4, CD8, CD3, Gr-1 and Mac-1. For staining purposes a cocktail of binding reagents, herein designated "lin", may be used. The lin panel will comprise binding reagents, e.g. antibodies and functional binding fragments thereof, ligands, peptidomimetics, etc., that recognize two or more of the lineage markers. A lin panel will generally include at least one marker expressed on mature B cells, on mature T cells, on mature granulocytes and on mature macrophages. Markers suitable for use in a lineage panel are typically expressed on these mature cells, but are not present on multiple lineages, or on stem and progenitor cells.

The subject subsets are separated from a complex mixture of cells by techniques that enrich for cells having the above characteristics. For isolation of cells from tissue, an appropriate solution may be used for dispersion or suspension. Such solution will generally be a balanced salt solution, e.g. normal saline, PBS, Hank s balanced salt solution, etc., conveniently supplemented with fetal calf serum or other naturally occurring factors, in conjunction with an acceptable buffer at low concentration, generally from 5–25 mM. Convenient buffers include HEPES, phosphate buffers, lactate buffers, etc.

Separation of the subject cell populations will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbecco s Modified Eagle Medium (dMEM), Hank's Basic Salt Solution (HBSS), Dulbecco s phosphate buffered saline (dPBS), RPMI, Iscove s medium, PBS with 5 mM EDTA, etc., frequently supplemented with fetal calf serum, BSA, HSA, etc.

The labeled cells are then separated as to the expression of c-kit, IL-7Rα, and lin panel. The selected population is c-kit high, lin negative, IL-7Rα negative. Optionally the cell population is also divided into subsets based on expression of FcγR and CD34.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for myeloid progenitor activity are achieved in this manner. The subject population will be at or about 90% or more of the cell composition, and preferably be at or about 95% or more of the cell composition. The desired cells are identified by their surface phenotype, by the ability to respond to growth factors, and being able to provide for development in vivo and in vitro of multiple myeloid lineages. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors or stromal cells associated with hematopoietic cell proliferation and differentiation.

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5–10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Specific growth factors that may be used in culturing the subject cells include steel factor (c-kit ligand), Flk-2 ligand, IL-11, IL-3, GM-CSF, erythropoietin and thrombopoietin. The specific culture conditions are chosen to achieve a particular purpose, i.e. differentiation into erythroid of megakaryocyte populations, maintenance of progenitor cell activity, etc.

In addition to, or instead of growth factors, the subject cells may be grown in a co-culture with stromal or feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213–235) or "Dexter" culture conditions (Dexter et al. [1977] *J Exp Med* 145:1612–1616); and heterogeneous thymic stromal cells (Small and Weissman [1996] *Scand J Immunol* 44:115–121).

The subject cultured cells may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

The progenitor cells may be used in conjunction with the culture system in the isolation and evaluation of factors associated with the differentiation and maturation of lymphoid cells. Thus, the progenitor cells may be used in assays to determine the activity of media, such as conditioned media, evaluate fluids for growth factor activity, involvement with dedication of lineages, or the like.

The subject CMP, MEP and/or GMP populations may be used for reconstitution of myeloid function in a recipient, e.g. platelets, megakaryocytes, neutrophils, monocytes, macrophages and erythroid cells. The condition may be caused by genetic or environmental conditions, e.g. infection with a pathogen such as HIV, exposure to radiation, etc. Autologous cells, particularly if removed prior to cytoreductive or other therapy, or allogeneic cells, may be used for progenitor cell isolation and subsequent transplantation.

Genes may be introduced into the myeloid progenitor cells for a variety of purposes, e.g. prevent HIV infection, replace genes having a loss of function mutation, provide recognition of a particular antigen, suppress activation of a particular antigen receptor, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are hematopoietic progenitor cells. For example, see Schwarzenberger et al. (1996) Blood 87:472–478; Nolta et al. (1996) *P.N.A.S.* 93:2414–2419; and Maze et al. (1996) *P.N.A.S.* 93:206–210.

Combinations of retroviruses and an appropriate packaging line may be used, where the capsid proteins will be functional for infecting the target cells. Usually, the cells and virus will be incubated for at least about 24 hours in the culture medium. The cells are then allowed to grow in the culture medium for short intervals in some applications, e.g. 24–73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

Lentiviral vectors such as those based on HIV or FIV gag sequences can be used to transfect non-dividing cells, such as the resting phase of human long term hematopoietic stem cells (see Uchida et al. (1998) *P.N.A.S.* 95(20):11939–44).

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) *P.N.A.S.* 90:8392–8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431 437); PA317 (Miller et al. (1986) *Mol. Cell. Biol.* 6:2895 2902) GRIP (Danos et al. (1988) *PNAS* 85:6460 6464). Retroviruses packaged with xenotropic envelope protein, e.g. AKR env, are capable of infecting most mammalian cell types, except murine cells.

The sequences at the 5 and 3 termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5 LTR acts as a strong promoter, driving transcription of the introduced gene after integration into a target cell genome. For some uses, however, it is desirable to have a regulatable promoter driving expression. Where such a promoter is included, the promoter function of the LTR will be inactivated. This is accomplished by a deletion of the U3 region in the 3 LTR, including the enhancer repeats and promoter, that is sufficient to inactivate the promoter function. After integration into a target cell genome, there is a rearrangement of the 5 and 3 LTR, resulting in a transcriptionally defective provirus, termed a "self-inactivating vector".

The vectors may include genes that must later be removed, e.g. using a recombinase system such as Cre/Lox, or the cells that express them destroyed, e.g. by including genes that allow selective toxicity such as herpesvirus TK, bcl-xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types.

To prove that one has genetically modified progenitor cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the myeloid lineages while maintaining the ability to express the introduced DNA. Various tests in vitro and in vivo may be employed to ensure that the pluripotent capability of the cells has been maintained.

The progenitor cells may be administered in any physiologically acceptable medium, normally intravascularly, although they may also be introduced into bone or other convenient site, where the cells may find an appropriate site for regeneration and differentiation. Usually, at least $1\times10^5$ cells will be administered, preferably $1\times10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

The subject cells are useful for in vitro assays and screening to detect factors that are active on myeloid progenitors, particularly those that are specific for myeloid, including megakaryocytic and erythroid lineages, and do not affect lymphoid cells. Of particular interest are screening assays for agents that are active on human cells. A wide variety of assays may be used for this purpose, including immunoassays for protein binding; determination of cell growth, differentiation and functional activity; production of cytokines, e.g. IL-1; and the like.

Of particular interest is the examination of gene expression in the myeloid progenitor subsets of the invention. The expressed set of genes may be compared between the myeloid progenitor subsets, or against other hematopoietic subsets as known in the art. For example, in order to determine the genes that are regulated during megakaryocyte development, one could compare the set of genes expressed in the MEP progenitor set with the CMP, or the GM progenitors, or against stem cell or lymphoid progenitor cells.

Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+mRNA. One of skill in the art can readily use these methods to determine differences in the size or amount of mRNA transcripts between two samples. For example, the level of particular mRNAs in MEP cells is compared with the expression of the mRNAs in a reference sample, e.g. CMP cells.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an arrays are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800, 992.

In another screening method, the test sample is assayed for the level of a CMP sequences polypeptide. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed. polypeptide can be used, for example ELISA, western blot, immunoprecipitation, radioimmunoassay, etc.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

EXAMPLE 1

Isolation of a Common Myeloid Progenitor

FIG. 1A shows the Sca-1/c-Kit expression profile of the lineage (Lin$^-$) IL-7R$\alpha^-$ fraction. In vitro, myeloerythroid colony-forming unit (CFU) activity was exclusively found in the c-Kit$^+$, but not the c-Kit$^-$ fraction. The Lin$^-$ IL-7R$\alpha^-$ c-Kit$^+$ cells contained Sca-1$^+$ and Sca-1$^-$ cells. The Lin$^-$IL-7R$\alpha^{31}$ Sca-1$^+$ c-Kit$^+$ population is highly enriched for HSC1-3, and a majority of the HSC population were Fc receptor γ II/III (FcγR)$^{lo}$ CD34$^+$. On the other hand, the Lin$^-$ IL-7R$\alpha^-$ Sca-1$^-$ c-Kit$^+$ cells were subdivided into three subpopulations according to the expression profile of FcγR and CD34; FcγR$^{lo}$CD34$^+$, FcγR$^{lo}$ CD34$^-$ and FcγR$^{hi}$ CD34$^+$ populations (FIG. 1B). The CSF-1 receptor (macrophage-CSF receptor {M-CSFR}), granulocyte-CSF receptor (G-CSFR), and the common β chain (βc) (the indispensable subunit of the receptors for IL-3, IL-5 and granulocyte/macrophage colony-stimulating factor {GM-CSF}), were most highly expressed in the FcγR$^{hi}$ population, suggesting that the FcγR$^{hi}$CD34$^+$ cells are committed to the granulocyte/macrophage lineages (FIG. 1B).

Figure 2B:
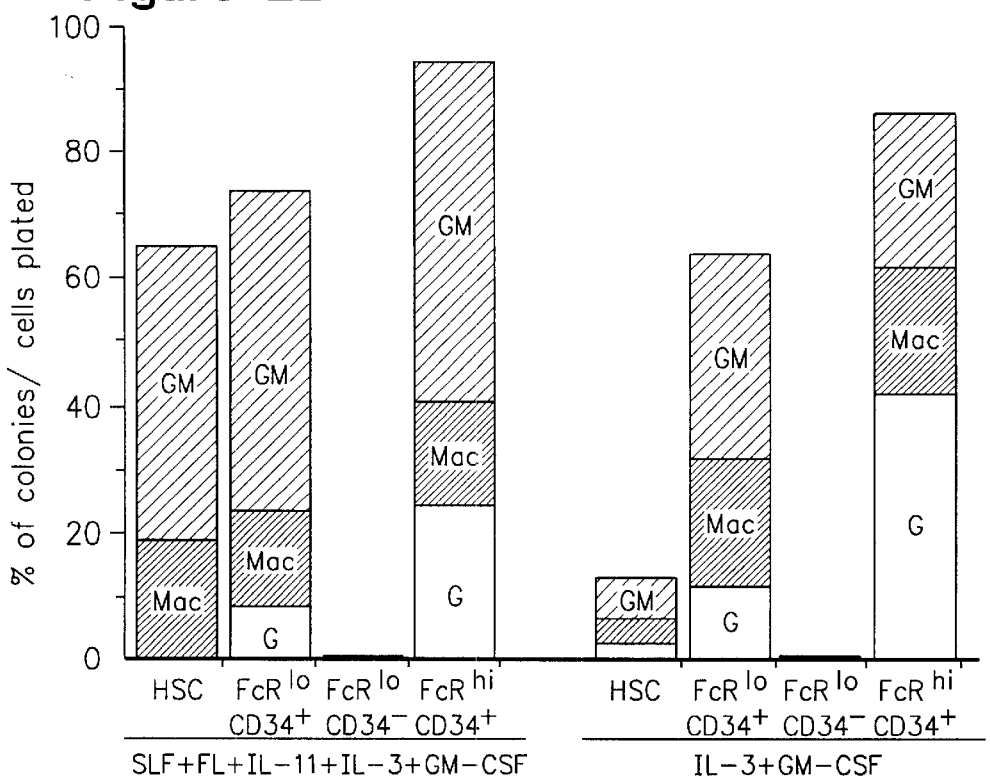
Figure 3:
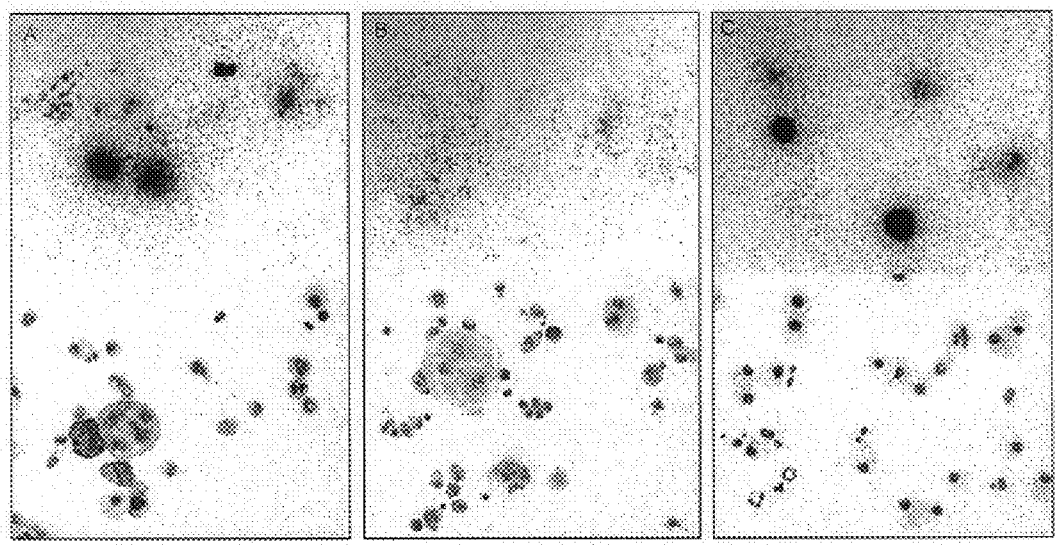
FIG. 3. Morphology of day 7 colonies derived from sorted myeloid progenitors. Two hundred cells from each population were cultured in methylcellulose containing SLF, IL-3, IL-11, GM-CSF, Epo and Tpo in 35 mm dishes. Upper panels show the appearance of colonies derived from FcγR$^{lo}$ CD34$^+$ CMP (A), FcγR$^{lo}$ CD34$^-$ MEP progenitors (B), and FcγR$^{hi}$CD34$^+$ G/M progenitors (C). The bottom panels show the cellular morphology from 5 pooled colonies collected from each culture (Giemsa staining 1000X).

The methylcellulose CFU activity for each of the above populations is shown in FIGS. 2 and 3. In the presence of steel factor (SLF), flt-3 ligand (FL), interleukin (IL)-3, IL-11, GM-CSF, thrombopoietin (Tpo) and erythropoietin (Epo), >90% of single-sorted FcγR$^{lo}$CD34$^+$ cells gave rise to various types of myeloerythroid colonies including CFU-GEMMeg, burst-forming unit-erythroid (BFU-E), CFU-megakaryocytes (CFU-Meg), CFU-granulocyte/macrophage (CFU-GM), CFU-granulocyte (CFU-G) and CFU-macrophage (CFU-M). Strikingly, the FcγR$^{hi}$CD34$^+$ population generated only CFU-M, CFU-G, or CFU-GM colonies containing macrophages and/or granulocytes in response to any of the growth factor combinations. In contrast, FcγR$^{lo}$CD34$^-$ cells strictly gave rise to CFU-Meg, BFU-E, or CFU-MEP colonies containing only megakaryocytes and/or erythrocytes in response to IL-3, GM-CSF, Tpo and Epo, but did not form colonies in the absence of Tpo and Epo. All three myeloid progenitor populations do not require "early-acting cytokines" such as SLF, FL and IL-11 to initiate colony formation, whereas HSC are largely dependent on these cytokines.

Figure 4:
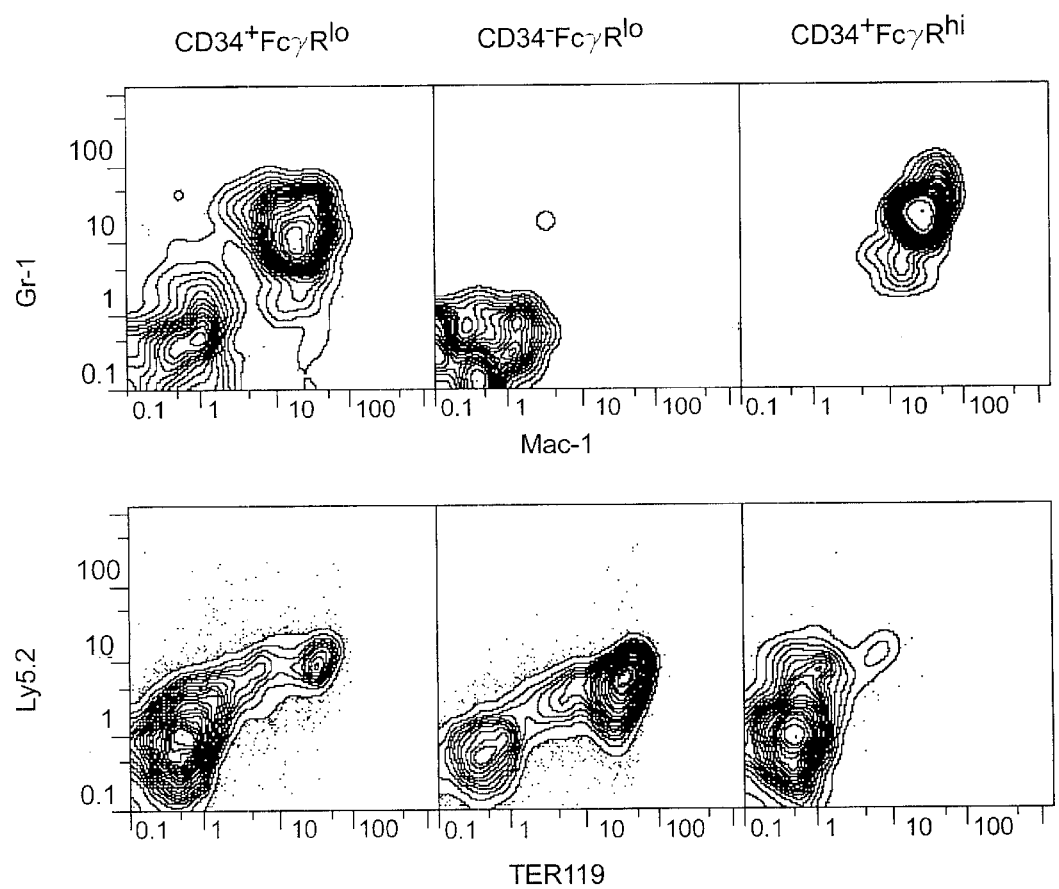
FIG. 4. In vivo differentiation potential of myeloid progenitors. Splenocytes from lethally-irradiated congenic recipient mice were analyzed six days after the intravenous injection of either 10,000 CMP, Meg/E or GMP progenitors. Upper panels show the Mac-1/Gr-1 profiles of donor-derived cells (CD45.1) in recipient mice (CD45.2). Lower panels show CD45.1/TER119 profiles from the Mac-1-Gr-1-fractions shown above.

All of these progenitors showed rapid differentiation activity in vivo (FIG. 4). Six days after the injection of 10,000 FcγR$^{lo}$ CD34$^+$ cells into lethally-irradiated recipient mice, both Gr-1$^+$/Mac-1$^+$ myelomonocytic cells and TER119$^+$ erythroid cells were detectable in spleen and bone marrow. In contrast, 10,000 FcγR$^{hi}$ CD34$^+$ cells transiently gave rise to only Gr-1$^+$/Mac-1$^+$ cells whereas the FcγR$^{lo}$ CD34$^-$ population reconstituted only TER119$^+$ cells. Accordingly, the majority of day 8 spleen colony-forming unit (CFU-S) activity—comprised largely of erythroid cells—resided in the FcγR$^{lo}$ CD34$^-$ population (Table 1). FcγR$^{lo}$ CD34$^+$ cells gave rise to over four-fold fewer day 8 colonies while FcγR$^{hi}$ CD34$^+$ cells had no detectable activity. Some day 12 CFU-S—comprised of multipotent cells—also derived from FcγR$^{lo}$CD34$^-$ cells and FcγR$^{lo}$CD34$^+$ cells. These may be remnants of day 8 colonies, as previously described.

TABLE 1

| CFU-S Frequency of Hematopoietic Progenitor Populations | | | | |
|---|---|---|---|---|
| LT-HSC | ST-HSC | CMP | MEP-P | G/M-P |
| Day 12 | | | | |
| 1/61* | 1/14* | 1/200 | 1/53 | <1/500 |
| Day 8 | | | | |
| <1/100* | <1/100* | 1/67 | 1/15 | <1/500 |

*These data from Morrison and Weissman and are presented for comparison.

To evaluate self-renewal and proliferative capacity, we co-injected 200 HSC (CD45.2–C57B6) with 5,000 cells of each myeloid progenitor (CD45.1–C57B6) into lethally-irradiated CD45.2–C57B6 hosts. In this competitive reconstitution assay, the progeny from either FcγR$^{lo}$ CD34$^-$ or FcγR$^{hi}$ CD34$^+$ cells were undetectable after two weeks. The myeloid progeny from FcγR$^{lo}$ CD34$^+$ cells were detectable at two weeks after injection, but disappeared by three weeks post-injection. This suggests that these populations have no or limited self-renewal activity. These results are consistent with our previous findings that HSC contained within bone marrow transplants are responsible for the majority of white blood cells, platelets, and red blood cells produced after two weeks post-transplantation. We could not detect B cell or T cell differentiation from either the FcγR$^{lo}$ CD34$^-$ or the FcγR$^{hi}$ CD34$^+$ population in competitive reconstitution or intrathymic injection assays. The FcγR$^{lo}$ CD34$^+$ population could not generate T cells, but 1 in 2,800 cells in the FcγR$^{lo}$ CD34$^+$ fraction differentiated into B cells in vitro by the method previously reported. The B cell readout from CLP in this assay is 1 in 6 cells. Thus, the low frequency of B cell readout from the FcγR$^{lo}$ CD34$^+$ population likely reflects minor contamination of a B cell-committed progenitor with a similar cell-surface phenotype that only becomes apparent when large numbers of cells are sorted.

Figure 5A:
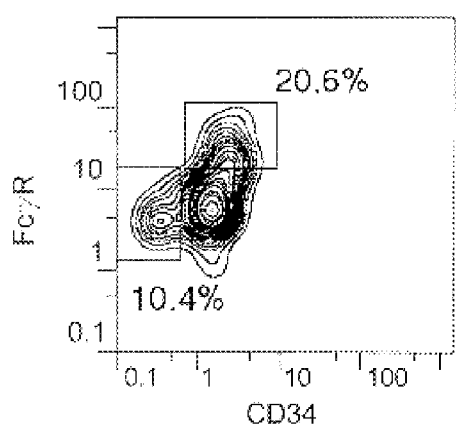
FIG. 5. Lineage relationships among the myeloid progenitor subsets. (A) FcγR$^{lo}$ CD34$^+$ CMP gave rise to FcγR$^{lo}$ CD34$^-$ MEP progenitors and FcγR$^{hi}$CD34$^+$ G/M progenitors 60 hr after sorting onto S17 stromal layers. (B) RT-PCR for GATA-1 and Epo-R expression. Low expression is seen in FcgR$^{lo}$ CD34$^+$ CMP, and is most pronounced in the FcγR$^{lo}$ CD34$^-$ MEP progenitors. The FcγR$^{hi}$CD34$^+$ GMP progenitors do not express either gene.

To test the lineage relationships among these three myeloid progenitor populations, we cultured each population on S17 stromal layers for 60 hrs and analyzed their phenotypic changes by flow cytometry. The FcγR$^{lo}$ CD34$^+$ cells gave rise to FcγR$^{lo}$ CD34$^-$ cells and FcγR$^{hi}$ CD34$^+$ cells (FIG. 5A). Resorted FcγR$^{lo}$ CD34$^-$ cells and FcγR$^{hi}$CD34$^+$ cells derived from FcγR$^{lo}$CD34$^+$ cells formed MEP and G/M colonies in methylcellulose, respectively. In contrast, neither FcγR$^{lo}$ CD34$^-$ nor FcγR$^{hi}$ CD34$^+$ cells gave rise to the other two progenitor subtypes; progeny from both populations rapidly down regulated c-Kit expression and differentiated into mature cell types. Thus, the FcγR$^{lo}$ CD34$^+$ CMP is upstream of both FcγR$^{lo}$ CD34$^-$ and FcγR$^{hi}$ CD34+ cells that are committed to the MEP and G/M lineages, respectively.

Figure 5B:
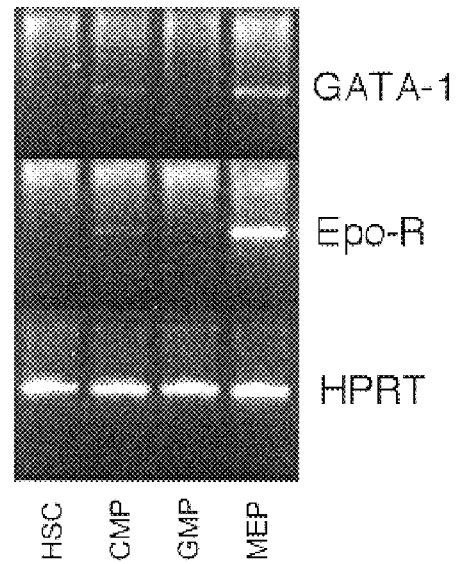

Among various transcription factors, GATA-1 has been shown to play a critical role in the commitment of multipotent progenitors to the erythroid and megakaryocytic lineages through activation of the Epo receptor (Epo-R) promotor. The expression of GATA-1 was detectable in the FcγR$^{lo}$ CD34+ CMP, and was highly pronounced in the FcγR$^{lo}$ CD34− MEP progenitors (FIG. 5B). In contrast, neither FcγR$^{hi}$ CD34+ G/M progenitors nor HSC expressed detectable levels of GATA-1. The expression pattern of the Epo-R correlated with that of GATA-1.

Recloning studies using multipotent colony-forming cells suggest that myeloid commitment is an asymmetric event, and that lineage commitment does not necessarily follow a specific pattern in vitro. The identification of a common myeloid progenitor, in addition to the common lymphoid progenitor suggests that commitment to the myeloid or lymphoid lineages occurs relatively early following HSC differentiation. The restricted differentiation capacity, both in vitro and in vivo, to either the myeloid or lymphoid lineages from each progenitor also suggests that significant cross-talk or plasticity across these lineages is rare once HSC differentiate to these points. Likewise, the restricted differentiation capacity of the CMP to either the erythroid/megakaryocytic or myelomonocytic lineages suggests that this developmental choice is specifically regulated and may involve differential expression of genes controlling transcription such as GATA-1. The discovery of the CMP, as well as its lineage-restricted descendants should provide the means to study the molecular events underlying lineage determination, test whether lineage commitment is stochastic or instructive, and may better our understanding of how specific lineages are affected in the nonlymphoid leukemias.

Methods

Mouse Strains

The congenic strains of mice, C57BL/Ka-Thy1.1 (CD45.2) and C57BL/Ka-Thy1.1-CD45.1 mice were used as described. C57BL/6 RAG-2-/-(CD45.2) mice were generated by crossing C57BL/6 RAG-2-/-(CD45.1) mice with C57BL/6-CD45.2 mice. The C57BL/6 RAG-2-/-(CD45.2) mice were used as recipients.

Cell Staining and Sorting

Bone marrow cells were stained with biotinylated antibodies specific for lineage (Lin) markers (CD3: KT31.1, CD4: GK1.5, CD8: 53-6.7, B220: 6B2, Gr-1: 8C5, TER119, and CD19: 1D3, IgM: R6-60.2(Pharmingen)), and IL-7Rα (A7R34). Lin+ cells were partially removed with sheep anti-rat IgG conjugated immuno-magnetic beads (Dynabeads M450, Dynal A.S., Oslo, Norway), and the remaining cells were stained with avidin-Cy5-PE (Tricolor) (Caltag, Burlingame, Calif.). Cells were stained with PE-conjugated anti-FcγR (2.4G2), FITC-conjugated CD34 (RAM34) (Pharmingen), Texas red-conjugated anti-Sca-1 (E13-161-7) and APC-conjugated anti-c-Kit (2B8) monoclonal antibodies. FITC-conjugated anti-common β chain (9D3) antibodies, and rabbit anti-M-CSFR antibodies were also used. Cells were sorted or analyzed as previously described (Kondo et al. (1997) supra.)

In vivo and in vitro Assays Determine Differentiation Potential of Progenitors.

For reconstitution assays, purified progenitors were injected into the retro-orbital venous sinus of lethally-irradiated (920 RAD) congenic mice, that differed only at the CD45 allele, together with 200 host-type HSC. RAG-2-/-recipients received 400 RAD. Intrathymic injections were as described (Kondo et al. (1997), supra.) CFU-S assays Were performed with 100–500 double-sorted progenitors/mouse as previously described (Traver et al. (1998), supra.)

Evaluation of myeloid colony formation was performed by a methyl-cellulose assay previously reported (Morrison et al. (1996), supra.) Cytokines such as mouse SLF (20 ng/ml), mouse IL-3 (30 ng/ml), mouse IL-11 (10 ng/ml), mouse GM-CSF (10 ng/ml), mouse Tpo (10 ng/ml) and human Epo (1 U/ml) were purchased from R&D systems (Minneapolis, Minn.). Progenitors were also cultured on irradiated (3,000 rad)-S17 stromal cell layers in 24-well plates with RPMI 1640 medium containing 10% FBS (Gemini Bioproduct, Calabasas, Calif.) and mouse IL-7 (10 ng/ml). All cultures were incubated at 37+ C. in a humidified chamber under 7% CO2.

Evaluation of GATA-1 and Epo-R Expression mRNA was purified from 10,000 cells from each population, and was amplified by RT-PCR. Primer sequences used for (SEQ ID NO:1) GATA-1: 5'-GGAATTCGGGCCCCTTGTGAGGCCAGAGAG-3' and (SEQ ID NO:2) 5'-CGGGGTACCTCACGCTCCAGCCAGATTCGACCC-3', for Epo-R: (SEQ ID NO:3) 5'-ATGCCTGTAATCCCAGCACT-3' and (SEQ ID NO:4) 5'-TCATGGTGGTAGCTGGTAGC-3', and for HPRT: (SEQ ID NO:5) 5'-GTTCTTTGCTGACCTGCTGG-3' and (SEQ ID NO:6) 5'-TGGGGCTGTACTGCTTAACC-3'. Expected length of products are 375 bp, 581 bp and 400 bp, respectively. The samples were denatured (94° C., 30 sec), annealed (55° C., 2 min) and extended (72° C., 3 min) for 40 cycles.

All publications mentioned herein are incorporated herein by reference for the purpose of describing and disclosing, for example, the compounds and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A substantially pure composition of mammalian myeloid progenitor cells, wherein at least 95% of the cells in said composition are characterized as c-kit$^{hi}$, IL-7Rα$^-$, and lacking expression of the lineage specific markers B220, CD4, CD8, CD3, Gr-1 and Mac-1.

2. The composition of claim 1, wherein said myeloid progenitor cells are further characterized as FcγR$^{lo}$, CD34$^+$.

3. The composition of claim 1, wherein said myeloid progenitor cells are further characterized as FcγR$^{lo}$, CD34$^-$.

4. The composition of claim 1, wherein said myeloid progenitor cells are further characterized as FcγR$^{hi}$, CD34$^+$.

5. The composition of claim 1, wherein said cells are genetically modified to comprise an exogenous DNA vector.

6. A method of enrichment for a composition of mammalian myeloid progenitor cells, wherein at least 95% of the cells in said composition are characterized as c-kit$^{hi}$, IL-7Rα$^-$, and lacking expression of the lineage specific markers B220, CD4, CD8, CD3, Gr-1 and Mac-1, the method comprising:

combining reagents that specifically recognize c-kit, IL-7Rα and the lineage specific markers B220, CD4, CD8, CD3, Gr-1 and Mac-1 with a sample of hematopoietic cells; and selecting for those cells that are c-kit$^{hi}$, IL-7Rα$^-$, and lacking expression of the lineage specific markers B220, CD4, CD8, CD3, Gr-1 and Mac-1, to provide an enriched population of cells having myeloid lineage progenitor activity.

7. A method according to claim 6, wherein said sample of hematopoietic cells is bone marrow.

8. A method according to claim 7, wherein said sample of hematopoietic cells is mobilized peripheral blood.

9. The method according to claim 7, wherein said cells are mouse cells, and further comprising the steps of:

combining reagents that specifically recognize Sca-1 with said sample of hematopoietic cells; and selecting for those cells that are Sca-1$^-$.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Homo sapiens

```
<400> SEQUENCE: 1
ggaattcggg ccccttgtga ggccagagag                                    30

<210> SEQ ID NO 2
<211> LENGTH: 33
<212> TYPE: DNA
<213> ORGANISM: Homo sapiens

<400> SEQUENCE: 2
cggggtacct cacgctccag ccagattcga ccc                                33

<210> SEQ ID NO 3
<211> LENGTH: 20
<212> TYPE: DNA
<213> ORGANISM: Homo sapiens

<400> SEQUENCE: 3
atgcctgtaa tcccagcact                                               20

<210> SEQ ID NO 4
<211> LENGTH: 20
<212> TYPE: DNA
<213> ORGANISM: Homo sapiens

<400> SEQUENCE: 4
tcatggtggt agctggtagc                                               20

<210> SEQ ID NO 5
<211> LENGTH: 20
<212> TYPE: DNA
<213> ORGANISM: Homo sapiens

<400> SEQUENCE: 5
gttctttgct gacctgctgg                                               20

<210> SEQ ID NO 6
<211> LENGTH: 20
<212> TYPE: DNA
<213> ORGANISM: Homo sapiens

<400> SEQUENCE: 6
tggggctgta ctgcttaacc                                               20
```